United States Patent
Welch et al.

(10) Patent No.: US 7,179,269 B2
(45) Date of Patent: Feb. 20, 2007

(54) APPARATUS AND SYSTEM FOR REMOVING AN OBSTRUCTION FROM A LUMEN

(75) Inventors: Eric Welch, Miramar, FL (US); Erice N. Hubbart, Mattapan, MA (US); Michael J. Voss, Weston, FL (US); Robert B. DeVries, Marlborough, MA (US); Paul DiCarlo, Middleboro, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 390 days.

(21) Appl. No.: 10/152,129

(22) Filed: May 20, 2002

(65) Prior Publication Data

US 2003/0216760 A1 Nov. 20, 2003

(51) Int. Cl.
*A61B 17/22* (2006.01)
(52) U.S. Cl. .......................... 606/159; 604/43
(58) Field of Classification Search ............... 606/127, 606/128, 159, 170, 180; 604/43
See application file for complete search history.

(56) References Cited

U.S. PATENT DOCUMENTS

| | | |
|---|---|---|
| 1,112,982 A | 10/1914 | Conine |
| 1,612,697 A | 12/1926 | Cecil |
| 2,701,559 A | 2/1955 | Cooper |
| 3,352,303 A | 11/1967 | Delaney |
| 3,614,953 A | 10/1971 | Moss |
| 3,894,673 A | 7/1975 | Lowder et al. |
| 3,896,815 A | 7/1975 | Fettel et al. |
| 4,018,576 A | 4/1977 | Lowder et al. |
| 4,273,128 A | 6/1981 | Lary |
| 4,443,488 A | 4/1984 | Little et al. |
| 4,445,509 A | 5/1984 | Auth |
| 4,465,072 A | 8/1984 | Taheri |

(Continued)

FOREIGN PATENT DOCUMENTS

DE 867 144 2/1953

(Continued)

OTHER PUBLICATIONS

Product information for Oasis™ Thrombectomy System. © 1999. Boston Scientific Corporation.

*Primary Examiner*—Michael J. Hayes
*Assistant Examiner*—Nguyen Victor
(74) *Attorney, Agent, or Firm*—Crompton, Seager & Tufte LLC

(57) ABSTRACT

An apparatus and system for removing an obstruction from a body lumen simultaneously mechanically dislodges the obstruction, macerates the obstruction, and aspirates the effluent caused thereby. The maceration is effected by directing pressurized fluid to the obstruction, while the obstruction is dislodged by a tip portion formed on the end of a guidewire. The apparatus includes a flexible catheter having at least two channels individually accommodating fluid flow paths towards and away from the obstruction. The guidewire may be disposed in either of the channels or a third channel formed in the flexible catheter. The apparatus also includes a drive unit for rotating the guidewire. The drive unit may be an external drive unit, such as an electrical motor, or may include drive elements formed on the guidewire within a drive chamber, across which the fluid flows and imparts energy against the drive elements to cause rotation of the guidewire.

14 Claims, 7 Drawing Sheets

U.S. PATENT DOCUMENTS

| | | | |
|---|---|---|---|
| 4,496,347 A | 1/1985 | MacLean et al. | |
| 4,530,125 A | 7/1985 | Hofmann | |
| 4,572,186 A | 2/1986 | Gould et al. | |
| 4,589,412 A | 5/1986 | Kensey | |
| 4,631,052 A | 12/1986 | Kensey | |
| 4,636,200 A | 1/1987 | Vaillancourt | |
| 4,646,736 A | 3/1987 | Auth | |
| 4,650,466 A | 3/1987 | Luther | |
| 4,653,496 A | 3/1987 | Bundy et al. | |
| 4,679,557 A | 7/1987 | Opie et al. | |
| 4,685,458 A | 8/1987 | Leckrone | |
| 4,690,672 A | 9/1987 | Veltrup | |
| 4,696,667 A | 9/1987 | Masch | |
| 4,725,264 A | 2/1988 | Glassman | |
| 4,728,319 A | 3/1988 | Masch | |
| 4,732,154 A | 3/1988 | Shiber | |
| 4,743,943 A | 5/1988 | Adams, Jr. et al. | |
| 4,747,821 A | 5/1988 | Kensey et al. | |
| 4,765,332 A | 8/1988 | Fischell et al. | |
| 4,771,774 A | 9/1988 | Simpson et al. | |
| 4,781,186 A | 11/1988 | Simpson et al. | |
| 4,784,636 A | 11/1988 | Rydell | |
| 4,790,813 A | 12/1988 | Kensey | |
| 4,794,928 A | 1/1989 | Kletschka | |
| 4,794,931 A | 1/1989 | Yock | |
| 4,842,579 A | 6/1989 | Shiber | |
| 4,850,957 A | 7/1989 | Summers | |
| 4,857,045 A | 8/1989 | Rydell | |
| 4,885,003 A | 12/1989 | Hillstead | |
| 4,886,061 A | 12/1989 | Fischell et al. | |
| 4,895,560 A | 1/1990 | Papantonakos | |
| 4,898,574 A | 2/1990 | Uchiyama et al. | |
| 4,905,667 A | 3/1990 | Foerster et al. | |
| 4,921,484 A | 5/1990 | Hillstead | |
| 4,926,858 A | 5/1990 | Gifford, III et al. | |
| 4,950,238 A | 8/1990 | Sullivan | |
| 4,966,604 A | 10/1990 | Reiss | |
| 4,990,134 A | 2/1991 | Auth | |
| 4,994,067 A | 2/1991 | Summers | |
| RE33,569 E | 4/1991 | Gifford, III et al. | |
| 5,009,659 A | 4/1991 | Hamlin et al. | |
| 5,030,201 A | 7/1991 | Palestrant | |
| 5,034,001 A | 7/1991 | Garrison et al. | |
| 5,100,425 A | 3/1992 | Fischell et al. | |
| 5,116,350 A | 5/1992 | Stevens | |
| 5,135,483 A | 8/1992 | Wagner et al. | |
| 5,135,531 A | 8/1992 | Shiber | |
| 5,146,916 A | 9/1992 | Catalani | |
| 5,147,332 A | 9/1992 | Moorehead | |
| 5,154,724 A | 10/1992 | Andrews | |
| 5,167,622 A | 12/1992 | Muto | |
| 5,176,693 A | 1/1993 | Pannek, Jr. | |
| 5,192,291 A | 3/1993 | Pannek, Jr. | |
| 5,217,474 A | 6/1993 | Zacca et al. | |
| 5,223,309 A | 6/1993 | Farivar et al. | |
| 5,224,945 A | 7/1993 | Pannek, Jr. | |
| 5,250,060 A | 10/1993 | Carbo et al. | |
| 5,263,928 A | 11/1993 | Trauthen et al. | |
| 5,286,253 A | 2/1994 | Fucci | |
| 5,308,354 A | 5/1994 | Zacca et al. | |
| 5,314,407 A | 5/1994 | Auth et al. | |
| 5,314,438 A | 5/1994 | Shturman | |
| 5,318,518 A | 6/1994 | Plechinger et al. | |
| 5,318,576 A | 6/1994 | Plassche, Jr. et al. | |
| 5,320,599 A | 6/1994 | Griep et al. | |
| 5,324,263 A * | 6/1994 | Kraus et al. | 604/96.01 |
| 5,324,276 A | 6/1994 | Rosenberg | |
| 5,358,472 A * | 10/1994 | Vance et al. | 604/22 |
| 5,370,609 A | 12/1994 | Drasler et al. | |
| 5,372,587 A | 12/1994 | Hammerslag et al. | |
| 5,376,100 A | 12/1994 | Lefebvre | |
| 5,385,311 A | 1/1995 | Morikawa et al. | |
| 5,395,311 A | 3/1995 | Andrews | |
| 5,411,509 A | 5/1995 | Hilal | |
| 5,423,740 A * | 6/1995 | Sullivan et al. | 604/22 |
| 5,438,630 A | 8/1995 | Chen et al. | |
| 5,453,088 A | 9/1995 | Boudewijn et al. | |
| 5,457,841 A | 10/1995 | Minton | |
| 5,468,562 A | 11/1995 | Farivar et al. | |
| 5,490,859 A | 2/1996 | Mische et al. | |
| 5,496,267 A | 3/1996 | Drasler et al. | |
| 5,498,249 A | 3/1996 | Quinn | |
| 5,501,694 A | 3/1996 | Ressemann et al. | |
| 5,507,732 A | 4/1996 | McClure et al. | |
| 5,522,807 A | 6/1996 | Luther | |
| 5,527,292 A | 6/1996 | Adams et al. | |
| 5,536,234 A | 7/1996 | Newman | |
| 5,554,136 A | 9/1996 | Luther | |
| 5,556,405 A | 9/1996 | Lary | |
| 5,569,275 A | 10/1996 | Kotula et al. | |
| 5,569,276 A | 10/1996 | Jang et al. | |
| 5,571,086 A | 11/1996 | Kaplan et al. | |
| 5,584,843 A * | 12/1996 | Wulfman et al. | 606/159 |
| 5,603,703 A | 2/1997 | Elsberry et al. | |
| 5,649,941 A | 7/1997 | Lary | |
| 5,653,696 A | 8/1997 | Shiber | |
| 5,681,336 A | 10/1997 | Clement et al. | |
| 5,713,849 A * | 2/1998 | Bosma et al. | 604/28 |
| 5,725,543 A | 3/1998 | Redha | |
| 5,725,568 A | 3/1998 | Hastings | |
| 5,730,717 A | 3/1998 | Gelbfish | |
| 5,749,914 A | 5/1998 | Janssen | |
| 5,766,191 A | 6/1998 | Trerotola | |
| 5,766,192 A | 6/1998 | Zacca | |
| 5,772,627 A | 6/1998 | Acosta et al. | |
| 5,776,096 A | 7/1998 | Fields | |
| 5,779,721 A | 7/1998 | Nash | |
| 5,807,349 A | 9/1998 | Person et al. | |
| 5,816,923 A | 10/1998 | Milo et al. | |
| 5,842,479 A | 12/1998 | Plaia et al. | |
| 5,843,022 A | 12/1998 | Willard et al. | |
| 5,964,004 A | 10/1999 | Bean | |
| 5,984,904 A | 11/1999 | Steen et al. | |
| 6,013,020 A * | 1/2000 | Meloul et al. | 600/7 |
| 6,015,420 A | 1/2000 | Wulfman et al. | |
| 6,074,357 A | 6/2000 | Kaganov et al. | |
| 6,090,118 A | 7/2000 | McGuckin, Jr. | |
| 6,096,054 A | 8/2000 | Wyzgala et al. | |
| 6,129,698 A | 10/2000 | Beck | |
| 6,146,395 A | 11/2000 | Kanz et al. | |
| 6,152,909 A | 11/2000 | Bagaoisan et al. | |
| 6,152,913 A | 11/2000 | Feith et al. | |
| 6,159,195 A | 12/2000 | Ha et al. | |
| 6,183,487 B1 | 2/2001 | Barry et al. | |
| 6,259,938 B1 | 7/2001 | Zarychta et al. | |
| 6,270,509 B1 | 8/2001 | Barry et al. | |
| 6,280,432 B1 | 8/2001 | Turovskiy et al. | |
| 6,299,623 B1 | 10/2001 | Wulfman | |
| 6,344,049 B1 | 2/2002 | Levinson et al. | |
| 6,394,996 B1 | 5/2002 | Lawrence et al. | |
| 6,423,050 B1 | 7/2002 | Twardowski | |
| 6,451,036 B1 | 9/2002 | Heitzmann et al. | |
| 6,468,262 B1 | 10/2002 | Murphy | |
| 6,482,216 B1 | 11/2002 | Hiblar et al. | |
| 6,520,983 B1* | 2/2003 | Colgan et al. | 623/1.11 |
| 6,527,979 B2 | 3/2003 | Constantz et al. | |
| 6,579,298 B1 | 6/2003 | Bruneau et al. | |
| 6,632,230 B2 | 10/2003 | Barry | |
| 6,706,033 B1 | 3/2004 | Martinez et al. | |
| 6,764,494 B2 | 7/2004 | Menz et al. | |
| 6,849,068 B1 | 2/2005 | Bagaoisan et al. | |

| | 6,878,142 B2 | 4/2005 | Lawrence et al. |
|---|---|---|---|

FOREIGN PATENT DOCUMENTS

| EP | 0 086 048 A2 | 8/1983 |
|---|---|---|
| EP | 0 117 519 A1 | 9/1984 |
| EP | 0 268 228 A2 | 5/1988 |
| EP | 0 268 228 B1 | 5/1988 |
| EP | 0 427 368 A1 | 5/1991 |
| EP | 0 427 368 B1 | 5/1991 |
| GB | 2 020 557 A | 11/1979 |
| WO | WO 92/03097 A1 | 3/1992 |
| WO | WO 92/03098 A1 | 3/1992 |
| WO | WO 93/01753 A2 | 2/1993 |
| WO | WO 93/01753 A3 | 2/1993 |
| WO | WO 93/01849 A1 | 2/1993 |
| WO | WO 93/19679 A1 | 10/1993 |
| WO | WO 94/10919 A1 | 5/1994 |
| WO | WO 98/02101 A1 | 1/1998 |
| WO | WO 98/38928 A1 | 9/1998 |
| WO | WO 99/24320 A1 | 5/1999 |

* cited by examiner

APPARATUS AND SYSTEM FOR REMOVING AN OBSTRUCTION FROM A LUMEN

FIELD OF THE INVENTION

The present invention relates to removal of obstructions formed in a lumen and more particularly to the dislodgment and maceration of wall adherent thrombus in a body lumen and evacuation of the effluent resulting from the dislodgement and maceration.

BACKGROUND OF THE INVENTION

Thrombosis, the formation or presence of a blood clot inside a blood vessel or cavity of the heart, is a common but elusive illness that can result in suffering and death if not recognized and treated effectively. Thrombosis occurs in many individuals each year. Death can occur when thrombi break off and form pulmonary emboli, which pass to and obstruct the arteries of the lungs. Thrombosis and pulmonary embolism (PE) most often complicate the course of sick, hospitalized patients but may also affect ambulatory and otherwise healthy persons. It is estimated that each year numerous patients develop PE and that thousands die of this complication. PE is now the most frequent cause of death associated with childbirth.

A number of devices for use in a thrombectomy, a procedure to remove thrombus, have been proposed. Existing technology for the removal of thrombus formation may generally be categorized as suitable for removing either wall adherent thrombus or non-wall adherent thrombus. Devices for removing wall adherent thrombus effectively cut such thrombus into small fragments but do not remove it. Devices for removing non-wall adherent thrombus macerate and aspirate thrombus, but do not effectively remove wall adherent thrombus.

In addition to thrombosis, another major medical problem in the United States is heart disease produced by atherosclerosis. In atherosclerosis, plaque forms in an artery and can completely occlude the artery. If complete blockage occurs, stasis of blood can lead to thrombus formation along the arterial wall. The use of a balloon to open a closed body cavity has been used in the medical profession. The balloon is inserted during a percutaneous procedure. A potential advantage of balloon occlusion is that body cavity obstruction can be temporary; once the threat of embolization has subsided, the balloon can be deflated and removed.

Coronary angioplasty is accomplished using a balloon-tipped catheter inserted through an artery, typically in the groin or arm, to enlarge a narrowing in a coronary artery. Coronary artery disease occurs when cholesterol plaque builds up (as a result of atherosclerosis) in the walls of the arteries to the heart. Angioplasty is successful in opening coronary arteries in about 90% of patients but about 40% of patients with successful coronary angioplasty will develop recurrent narrowing at the site of balloon inflation (i.e., restenosis).

Other conditions face the medical industry in which it would be desirable to remove an obstruction, either adhered to a lumen wall or not, from the inside of the lumen. Such obstructions may be growths or deposits of tissue or cellular structures, such as gall stones and kidney stones. Obstructions may be found in the ducts and passages of the biliary, gastrointestinal, and urological systems, in addition to those found in the vasculature as mentioned above. In many cases, it would be desirable to utilize a device which is capable of simultaneously cutting the obstruction, macerating the obstruction, and aspirating the effluent caused by the cutting and maceration.

Each year, many people are diagnosed as having atherosclerotic heart disease and the other conditions mentioned above. In a population where life expectancy continues to increase, with a corresponding increase in atherosclerotic heart disease and ensuing thrombolytic conditions as well as the other conditions mentioned above, there is an urgent need for an inexpensive, efficient, safe and effective means for removing all types of obstructions, including wall adherent thrombus.

SUMMARY OF THE INVENTION

In view of the needs mentioned above and other objects, an embodiment of the present invention provides an apparatus for dislodging and macerating an obstruction, such as wall adherent thrombus, in a body lumen and for simultaneously aspirating the effluent created by the dislodging and maceration of the obstruction. The apparatus includes a catheter defining at least two channels individually accommodating inlet and return fluid flow paths, a guidewire longitudinally extending through one of the channels of the catheter, and a system for rotating the guidewire. The guidewire has a tip portion affixed to and extending beyond the distal end of the catheter for dislodging the obstruction upon rotation. The guidewire may be disposed in either of the two channels of the catheter accommodating either the inlet or return fluid flow paths or may be disposed in a third channel of the catheter dedicated solely to the guidewire.

According to another embodiment of the present invention, the system for rotating the guidewire utilizes the energy from the fluid flowing along the catheter. Such a system includes a housing defining a chamber having an inlet port for receiving fluid and a drive element affixed to a first segment of the guidewire located within the chamber. The chamber is in fluid flow communication with the first channel. Energy is transferred from the fluid flowing through the chamber to cause rotation of the guidewire. The system for rotating the guidewire may additionally or alternatively be an external driver, such as an electrical motor.

The tip portion according to the present invention may have a variety of configurations. The tip portion may have the shape of a spiral, a sine wave, a multiplane sine wave, a multiple coil, an oval, a basket comprising a plurality of ovals, a sphere comprising a plurality of circles, a helix, or a multi-helix. Alternatively, the tip portion may have the shape of a half sine wave, either adjacent the catheter or next to a tip portion with either a plain distal tip, an open loop distal tip, or a closed loop distal tip. In another alternative, the tip portion may have the shape of a sine wave. The tip portion may alternatively comprise a base filament and a plurality of cutting filaments extending perpendicularly from the base filament. Also, the tip portion may comprise a circular element and a plurality of cutting filaments extending radially outward from the circular element. A first radiopaque marker may be disposed at the proximal end of the tip portion and a second radiopaque marker may be disposed at the distal end of the tip portion.

According to an embodiment of the present invention, an apparatus for removing an obstruction from inside of a lumen comprises a catheter defining two channels, at least one fluid tube, a housing defining a chamber, a guidewire having a tip portion for dislodging the obstruction upon rotation, and a drive element. The obstruction may be wall adherent thrombus formed inside a body lumen or a previously implanted prosthetic component. The catheter includes a portion adapted for insertion into the lumen, and one of the channels of the catheter accommodates a return fluid flow path from the distal end of the catheter towards the proximal end. A fluid tube provides fluid to the chamber, which is interposed between and in fluid flow communication with the distal end of the fluid tube and the proximal end of either the first channel or a second fluid tube in the first channel. The guidewire longitudinally extends through the chamber and the second channel, with the tip portion extending beyond the distal end of the second channel. The drive element is affixed to a first segment of the guidewire which is located within the chamber. The drive element serves to transfer energy from the fluid flowing through the chamber to cause rotation of the guidewire.

In another embodiment of the present invention, the channel which accommodates the return fluid flow path also accommodates the guidewire. In an alternative embodiment, the channel which accommodates the guidewire is solely dedicated to accommodating the guidewire, and the other channel which accommodates the return fluid flow path also accommodates an inlet fluid tube for providing pressurized fluid to the lumen.

According to an embodiment of the present invention, a system for removing an obstruction from inside of a lumen includes the catheter, the guidewire with the affixed tip portion, and the means for rotating the guidewire, along with a fluid source coupled to the first channel for providing fluid, a fluid return tube connected to the catheter and in fluid communication with the return fluid flow path, a suction pump connected to the fluid return tube for creating a suction on the fluid as it returns through the return fluid flow path, and a tank connected to the output of the suction pump for receiving the fluid after it has passed through the fluid return tube.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1:
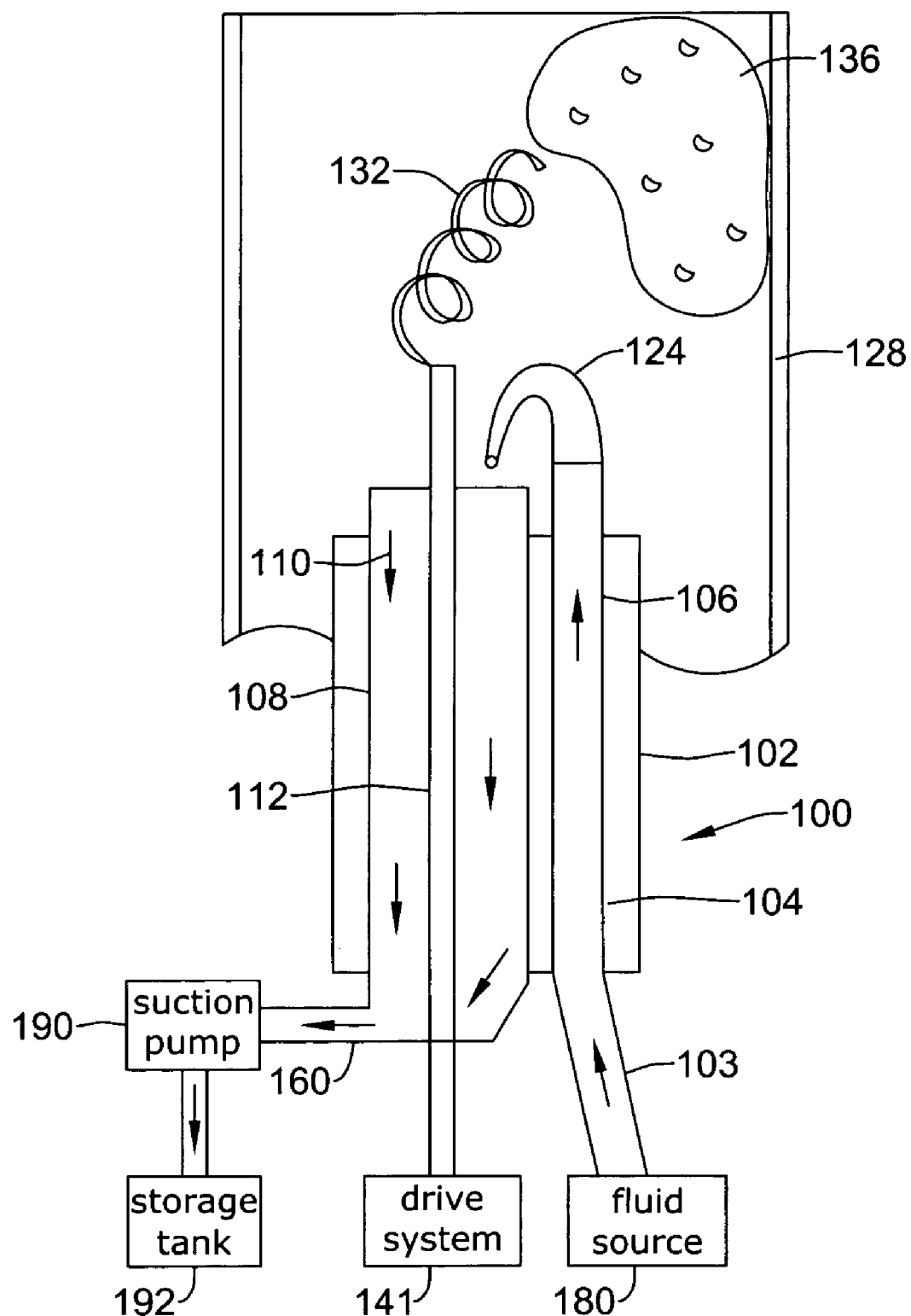
FIG. 1 is a longitudinal sectional view with a partial schematic, showing exemplary embodiments of the apparatus and system of the present invention.

In FIG. 1, there is shown an exemplary embodiment of the apparatus and system for removing an obstruction from the inside of a lumen. In the embodiment shown in FIG. 1, the lumen is a blood vessel 128, such as an artery, of a human body, although the apparatus and system of the present invention could be used to remove an obstruction in other types of body vessels or a previously deployed implant. The obstruction shown in FIG. 1 is thrombus 136, although the present invention is suitable for removing any of the obstructions mentioned above, including plaque, gall stones, kidney stones, or other growths or deposits of tissue or cellular structures, regardless of whether the obstruction is wall adherent or not. As used herein, when referring to "removing an obstruction," it should be recognized that this language contemplates both the removal of the entire obstruction or portions thereof, such that at least some improvement in patency of the lumen is achieved.

Referring to FIG. 1, the apparatus of the invention, as indicated by the reference numeral 100, includes a flexible catheter 102 that has been introduced into a blood vessel 128, such as a femoral artery, through an access point (not shown). Such access points are typically in the groin area of a patient, remote from the site of a blockage that has been determined to exist in the artery. Within the description of the invention, the word "distal" refers to a part of an item or a location that is further away from the access point, while the word "proximal" refers to a part of an item or a location that is closer to the access point. Such catheters are well-known in the art and can be made by known processes. For example, the catheter of the invention may be made of braided steel wire or PEBAX® amide copolymer. As is well known with such catheters, at least a portion of the catheter is adapted for insertion into the lumen. The method of introducing the apparatus of the present invention can be any well known percutaneous or "cut-down" procedure or a laparoscopic procedure.

The flexible catheter 102, preferably having a diameter of five to seven french when used to remove thrombus from the inside of an artery, defines a first channel 104 and a second channel 108 that provide passageways extending throughout the length of the flexible catheter 102, with each channel extending between a proximal end and a distal end generally parallel to a longitudinal axis. As shown in FIG. 1, the first channel 104 accommodates an inlet fluid flow path 106 from the proximal end of the catheter towards the distal end, for providing pressurized fluid flow into the lumen. The second channel 108 accommodates a return fluid flow path 110 from the distal end of the catheter towards the proximal end thereof. As will be discussed below, a separate polyimide inlet fluid tube may be disposed within first channel 104 or a nozzle 124 may be formed over first channel 104. In the case of a separate inlet fluid tube, the tube can be said to define the inlet fluid flow path when disposed in the first channel. As used herein, the term "channel" is meant to encompass both passages defined by the remaining solid material of the catheter radially surrounding the passages and passages formed by the placement of a smaller tube or catheter within a larger hollow catheter (such as the size of flexible catheter 102), which does not have such solid material throughout. The shapes of the cross-sections of the channels may be circular, ovular, crescent-shaped, or some other shape.

The apparatus 100 of the present invention also includes a guidewire 112 which extends longitudinally through the second channel 108 as shown in FIG. 1. The guidewire 112 terminates into a tip portion 132 (shown in various functional configurations in FIGS. 6–21, discussed below). Tip portion 132 is used to dislodge the obstruction upon rotation. By "dislodging," tip portion 132 can merely dislodge a non wall adherent obstruction from a lumen, but is preferably adapted to dislodge a wall adherent obstruction from a lumen. The phrase "dislodging the obstruction" contemplates dislodging an obstruction or cutting or fragmenting an obstruction into smaller pieces with at least some of the obstruction ready for further maceration or withdrawal from the lumen. In general, tip portion 132 upon rotation serves to dislodge in many ways, such as by cutting, agitating, fragmenting, and abrading either wall-adherent or non-wall-adherent material, and can be combined with the macerating effect of the spraying of a fluid. Tip portion 132 can either be formed integrally with guidewire 112 or can be made separately and later affixed to the distal end of guidewire 112. In operation, tip portion 132 and a segment of straight section of guidewire 112 extend beyond the distal end of the catheter 102 for a length as needed, depending on the location of the obstruction. Tip portion 132 is retractable into second channel 108 for aiding insertion of the catheter 102 into the body lumen. This axial movement of tip portion 132 can be achieved by sliding guidewire 112 relative to catheter 102. Other aspects of using a wire in a thrombectomy are described in U.S. Pat. No. 6,090,118, incorporated herein by reference.

The apparatus 100 of the present invention also includes a drive system 141 for rotating guidewire 112 to cause tip portion 132 to dislodge the obstruction. Drive system 141 could be any system or device used for imparting rotational movement to a guidewire or similar device. Preferably, drive system utilizes the energy from the fluid flowing along flexible catheter 102, as is described in connection with FIGS. 2–4. Alternatively, or in addition, drive system 141 may include external drivers, such as electrical motors, battery-powered motors, pneumatic drives, or hand-operated devices having gears. A one-way clutch may be incorporated to prevent the wire/drive from locking up if excessive resistance is 5 encountered. Preferably, drive system 141 is configured to impart axial movement to guidewire 112 in a controlled and precise manner.

FIG. 1 also shows a system for removing an obstruction from the inside of a lumen. In addition to the apparatus 100 as discussed above, the system of the present invention includes a fluid source 180 coupled to first channel 104 for providing fluid under pressure. Such a source is well known, and the fluid will vary with the particular application but, in many cases, is saline solution. The fluid source may be connected to first channel 104 by an input fluid tube 103. The system also includes a fluid return tube 160 connected to catheter 102 and in fluid communication with return fluid flow path 110. A suction pump 190 is connected to fluid return tube 160 and serves to create a suction on the fluid as it returns through the return fluid flow path and to aspirate any broken up portions of the obstruction (i.e., effluent) within the lumen. Finally, the system includes a storage tank 192 connected to the output of suction pump 190 for receiving the fluid after it has passed through the fluid return tube. Tank 192 is periodically drained, if needed. Flow arrows are shown in FIG. 1 of the fluid through inlet fluid flow path 106 and of the effluent through return fluid flow path 110.

Figure 2:
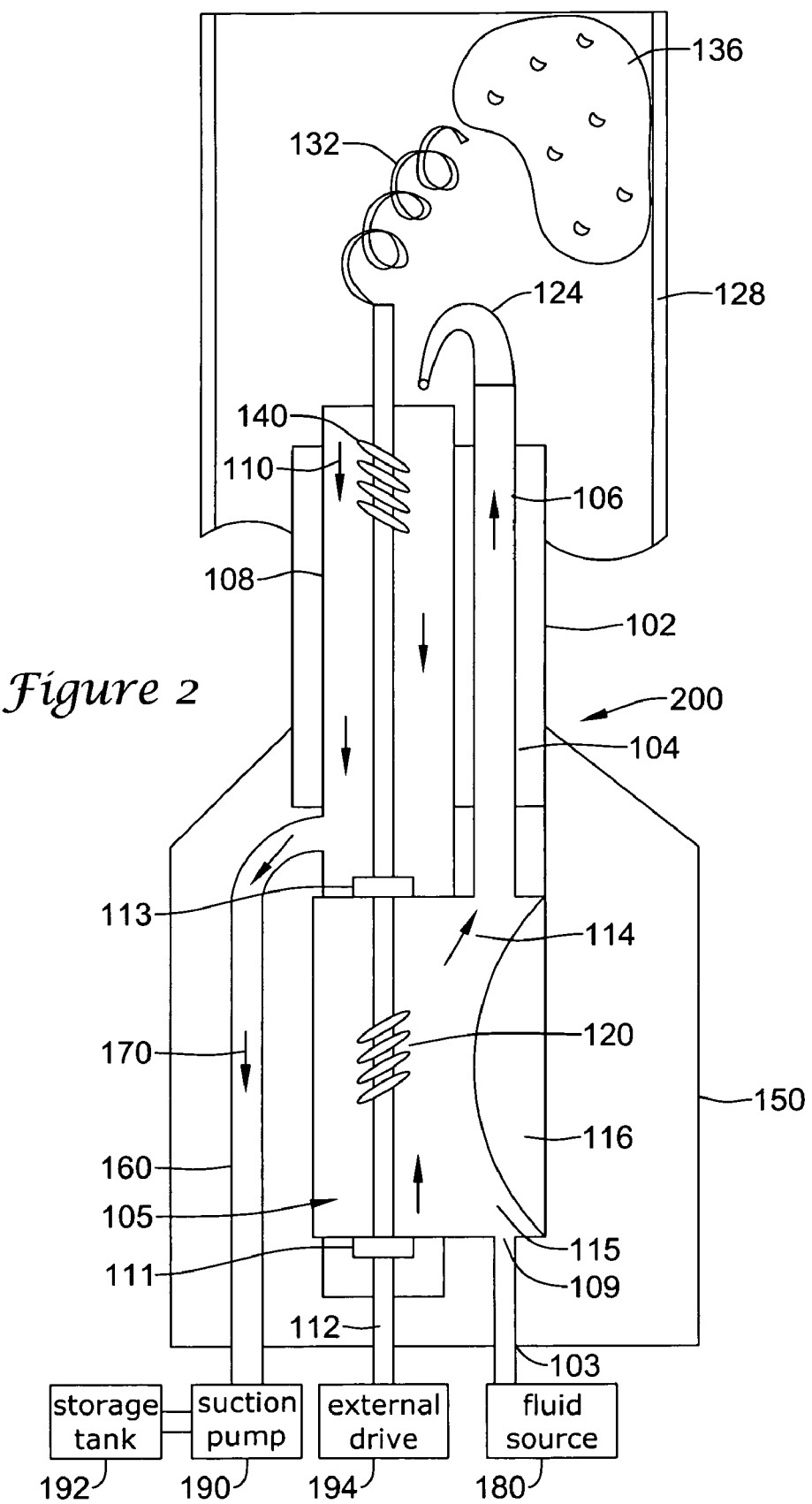
FIG. 2 is a longitudinal sectional view with a partial schematic, showing other exemplary embodiments of the apparatus and system of the present invention.

FIG. 2 shows an embodiment of the invention which has a configuration very similar to that shown in FIG. 1. The drive system of the apparatus shown in FIG. 2, however, is shown in more detail. For example, apparatus 200 of FIG. 2 shows a 25 housing which may be in the form of a handle 150. In the embodiments shown in FIGS. 2–4, the housing is in the form of a handle but the housing may be separate from the handle, which is designed to be grasped by a medical professional during operation of the apparatus of the present invention. Handle 150 (or a separate housing) defines a chamber 115 which is interposed between the distal end of an input 30 fluid tube 103 and the proximal end of first channel 104. As shown in FIG. 1, chamber 115 is coupled at its proximal end to input fluid tube 103 and at its distal end to first channel 104. Handle 150 may be coupled to catheter 102 in any known manner, such as by using a Luer lock. In operation, chamber 115 is in fluid flow communication with input fluid tube 103 and first channel 104 (or a separate inlet fluid tube disposed within first channel 104). A fluid source 180 may be connected to input fluid tube 103 for serving as the source of pressurized fluid, such as saline solution, for use in the invention as described herein. The housing has an inlet port 109 for receiving fluid from fluid source 180 and input fluid tube 103.

The chamber 115 is formed or configured to contain a drive element, such as a plurality of helical fins 120. The plurality of helical fins 120 are affixed to a guidewire 112 at a first segment of the guidewire within chamber 115, and are pitched to cause the guidewire 112 to rotate when the fluid flowing through the chamber impacts the plurality of helical fins 120. The guidewire 112 rotates clockwise (as viewed from the bottom) when the plurality of helical fins are pitched with a forward slope as shown in FIG. 1 and the rotation is counterclockwise when the plurality of helical fins are pitched with a backward slope. Although fins are shown to transfer the fluid force into rotational motion of the guidewire, it is foreseeable that one skilled in the art can use other similar approaches for self-rotating the guidewire with a suitable means of transfer of energy, such as the wind cups of a weather vane.

A flow restrictor 116 within chamber 115 is configured to control the velocity of the fluid flowing across chamber 115, without the need to change the input pressure from fluid source 180. As shown in FIG. 1, the shape of flow restrictor 116 is configured so that the cross-sectional area of chamber 115 is less at its mid-point than at its ends. Thus, the velocity of the fluid would be greater at its midpoint. Therefore, if needed, an operator could place plurality of fins 120 at the area of decreased cross-sectional area if a faster rate of rotation of the guidewire 112 is required. Other configurations of flow restrictor 116 can be used. For example, the material of flow restrictor 116 could be deformable so that, with radially inward pressure, an operator could reduce the cross-section of chamber 115 thereby increasing the velocity of the fluid at the appropriate point. The chamber 115 may have an adjustable cross-sectional for altering the fluid velocity and the speed of rotation of the guidewire by other ways also, by utilizing an adjusting screw around the chamber, for example.

Notwithstanding the rotatable feature of guidewire 112, a first seal 111 is formed around guidewire 112 for sealing engagement at the proximal end of chamber 115 and a second seal 113 is formed around guidewire 112 for sealing engagement at the distal end of chamber 115. Both first seal 111 and second seal 113 form a seal around guidewire 112 and, despite the passage of guidewire 112 through the chamber, inhibit fluid from flowing into or out of the chamber at these points. An inlet port 109 is formed in the housing for allowing fluid flow from input tube 103 into chamber 115.

Drive assembly 105 comprises the chamber 115 and the drive element, such as the fins 120, formed on the guidewire 112. As can be recognized, drive assembly 105 in conjunction with first channel 104, second channel 108, input fluid tube 103, and the seals 111 and 113, can be used in non-vascular applications, for example as a device for breaking up stones, fibrous tissue, cancerous cells, etc. FIG. 2 also shows a plurality of helical fins 140 which can be use as a suction device, as described in more detail below, either instead of or in addition to suction pump 190.

Referring to the operation of the embodiment shown in FIG. 2, flexible catheter 102 or a portion thereof is first introduced into a lumen to the desired location in a known way, with tip portion 132 retracted. After extending tip portion 132, fluid from fluid source 180 provides fluid under pressure. The pressure should be sufficient to cause rotation of guidewire 112, yet still have sufficient energy to cause micro-fragmenting of the thrombus and preferably create a Venturi effect at the distal end of flexible catheter 102. This will depend on a number of parameters, but the pressure will generally vary from 400 to 5,000 psi. More specifically, the pressure from fluid source 180 should be sufficient to allow for a pressure of at least 300 psi, preferably between 500 and 900 psi, of the fluid as it exits the distal end of first channel 104 into the lumen, taking into account pressure losses as the fluid travels from fluid source 180 to the lumen.

One such pressure loss is caused by the fluid imparting energy to the drive element (i.e., fins 120) to cause rotation of the guidewire 112. The fluid pressure should be sufficient to cause a rotational speed of the guidewire adequate to cut or break up the wall adherent thrombus. This rotational speed will vary depending on a number of factors, including the nature of the thrombus being removed, the shape of the tip portion, and the material used for the tip portion. Depending on these and other factors, the desired rotational speed of the guidewire is between 5 and 10,000 rpm, preferably between 60 and 5,000 rpm, and most preferably between 200 and 3,500 rpm.

The fluid flows, as shown by arrows 114, from fluid source 180 and through input fluid tube 103. It flows across inlet port 109 then enters chamber 115, where its velocity is increased due to the decreased cross-sectional area caused by flow restrictor 116. Upon impacting fins 120, it imparts some of its energy causing rotation of guidewire, thus causing tip portion 132 to dislodge the thrombus. As mentioned above, flow restrictor 116 is preferably a deformable material so that the cross-sectional area can be reduced during use, if an operator identifies the need to increase or decrease the rotational speed of the guidewire 112, without changing the pressure of the fluid from fluid source 180.

The fluid 114 then traverses from the chamber 115 into the first channel 104 and is therein designated as distal fluid flow through inlet fluid flow path 106. Distal fluid flow is, of course, still under positive pressure and is directed through the first channel distally past the distal end of the catheter out of the first channel 104 via nozzle 124, and returns to the flexible catheter 102 entering the second channel 108. The proximal end of nozzle 124 is shaped to mate with first channel 104. The nozzle 124 narrows and bends back toward its proximal end so that the downstream end of the nozzle will provide a spray of fluid back toward the distal end of the catheter, specifically towards the distal end of return fluid flow path 110.

The nozzle and return fluid flow path 110 are preferably sized to cause the fluid to micro-fragment and macerate thrombus 136, cut by tip portion 132, and simultaneously irrigate the area. As fluid leaves the nozzle 124, preferably a Venturi effect causes the fluid and effluent of the macerated thrombus 136 to mix together and to more efficiently enter the distal end of the return fluid flow path 110, which is an annulus around guidewire 112 in second channel 108. The Venturi effect occurs in a known way when fluid pressure drops as it is forced out the narrowed part of nozzle 124. When the fluid pressure drops below the pressure in the area adjacent to the nozzle 124, the thrombus in that adjacent area gets sprayed or mixed with the fluid, creating a mixture that travels through the intake of return fluid flow path 110 where it is channeled for discharge. The Venturi effect encourages the fluid and macerated thrombus to mix, resulting in a more homogeneous, easier flowing effluent. The fluid is channeled for discharge, and retains positive pressure as it traverses through the intake of return fluid flow path 110. Use of fluid flow in this manner, including the orientation of the nozzle, is described in U.S. Pat. No. 4,690,672, incorporated herein by reference. Preferably, flexible catheter 102 extends radially to the inner wall of blood vessel 128 to ensure that substantially all of the effluent is aspirated into second channel 108.

At the distal end of second channel 108, a supplemental element, such as a second plurality of fins 140, may optionally be affixed to guidewire 112, which is being rotated. The second plurality of fins 140 are configured to enhance or assist the flow of fluid which, after passing fins 140, can be characterized as micro-fragmented macerated thrombus effluent 170. The direction of the pitch of fins 140 should be opposite to that of fins 120; other characteristics of fins 140 can be readily selected by one skilled in the art to achieve the desired flow properties. Macerated thrombus effluent 170 continues to flow through return fluid flow path 110 of second channel 108 with the assistance of the increased pressure resulting from the rotation of the second segment of the plurality of fins 140.

Included within handle 150 is a fluid return tube 160 that is coupled to the return fluid flow path 110 on the distal end of chamber 115. Fluid return tube 160 may be a separate tube or may merely be a channel formed in the housing. Fluid return tube 160 extends longitudinally in a proximal direction and is used for discharging the effluent 170. A suction pump 190 may optionally be connected to the proximal end of fluid return tube 160 to assist the self-induced flow aided by fins 140. A storage tank 192 is connected to the output side of the suction pump 190 to capture the effluent 170 as it is removed from the body.

An external drive unit 194 may optionally be coupled to the guidewire 112. External drive 194 may be a pneumatic drive device, a battery-powered drive device, or an electrical drive device, such as an electrical motor. External drive unit 194 may be used to cause the guidewire 112 to rotate at times when it is not desirable to provide fluid to chamber 115. Also, external drive unit 194 may be connected to drive guidewire 112 axially over large or very small distances, requiring precise movements. The manner in which external drive unit 194 is connected to guidewire 112 is well-known in the art, and may be achieved by using a keyed connection or a pin vise connection.

Figure 3:
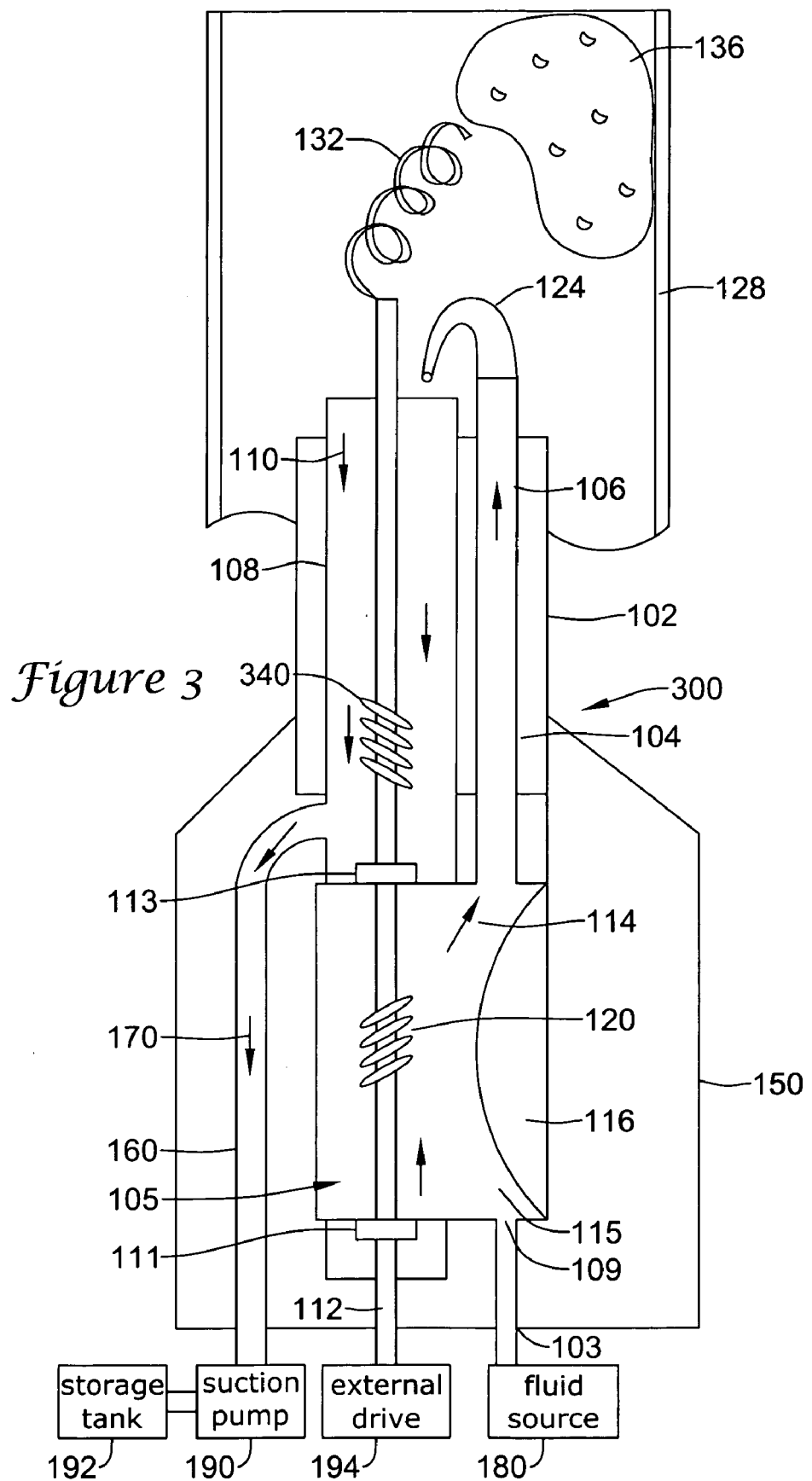
FIG. 3 is a longitudinal sectional view with a partial schematic, showing other exemplary embodiments of the apparatus and system of the present invention.

FIG. 3 illustrates another exemplary embodiment of the apparatus for removal of thrombus 136 from a blood vessel 128 of the human body. The apparatus of this embodiment is designated by the reference numeral 300. All of the features of the previous embodiments are incorporated in this embodiment with like elements having the same reference numerals. The following description is intended to disclose the different features of this embodiment and should be read with the features of the other embodiment of FIGS. 1 and 2 in mind.

As shown in FIG. 3, another drive element, such as another plurality of helical fins 340 is attached to guidewire 112. Second plurality of fins 340 is located near the proximal end of second channel 108 and adjacent to the distal end of the fluid return tube 160. Helical fins 340 rotate in the same direction as the first segment of the first plurality of fins 120 since both segment of fins are attached to guidewire 112. The rotational force is transferred from fins 120 through guidewire 112 and hence cause fins 340 to rotate in the same direction. The direction of the flow of fluid in return fluid flow path 110 is opposite the direction of the fluid flow in first channel 104 and the fins 340 are pitched so that any force on fins 340 will not oppose the direction of rotation that is caused by fins 120 relative to the direction of flow. The fins 340 are therefore oppositely slanted from fins 120 relative to the direction of flow.

The second segment of the plurality of fins 340 creates a vacuum, i.e. a space in which there is a low pressure, that provides a suction force to the flow of fluid 106 which after entering return fluid flow path 110 is redesignated as micro fragmented macerated thrombus effluent 170. Micro fragmented macerated thrombus effluent 170 is aided in its flow as a result of the suction resulting from the rotation of the second segment of the plurality of fins 340. Fluid return tube 160 extends longitudinally in a proximal direction and conducts the effluent 170 through to retainer tank 192. Suction pump 190 may be used to supplement the suction effect caused by plurality of fins 340.

An alternative embodiment of the invention is also possible when both the plurality of fins 140 and the plurality of fins 340 are used to provide a flow assist and a vacuum, respectively, so as to enhance the removal of the effluent 170 out through return tube 160. Again, in this embodiment, suction pump 190 is shown attached to the proximal end of return tube 160 and may be used, but is not needed. Another alternative embodiment for the removal of the effluent 170 out through return tube 160 is an embodiment in which suction pump 190 attached to the proximal end of return tube 160 is the only means of suction or assist provided to promote the removal of effluent 170 from return tube 160. As discussed above, external drive unit 194 may not be engaged if fluid source 180 is providing adequate rotational energy to fins 120.

Figure 4:
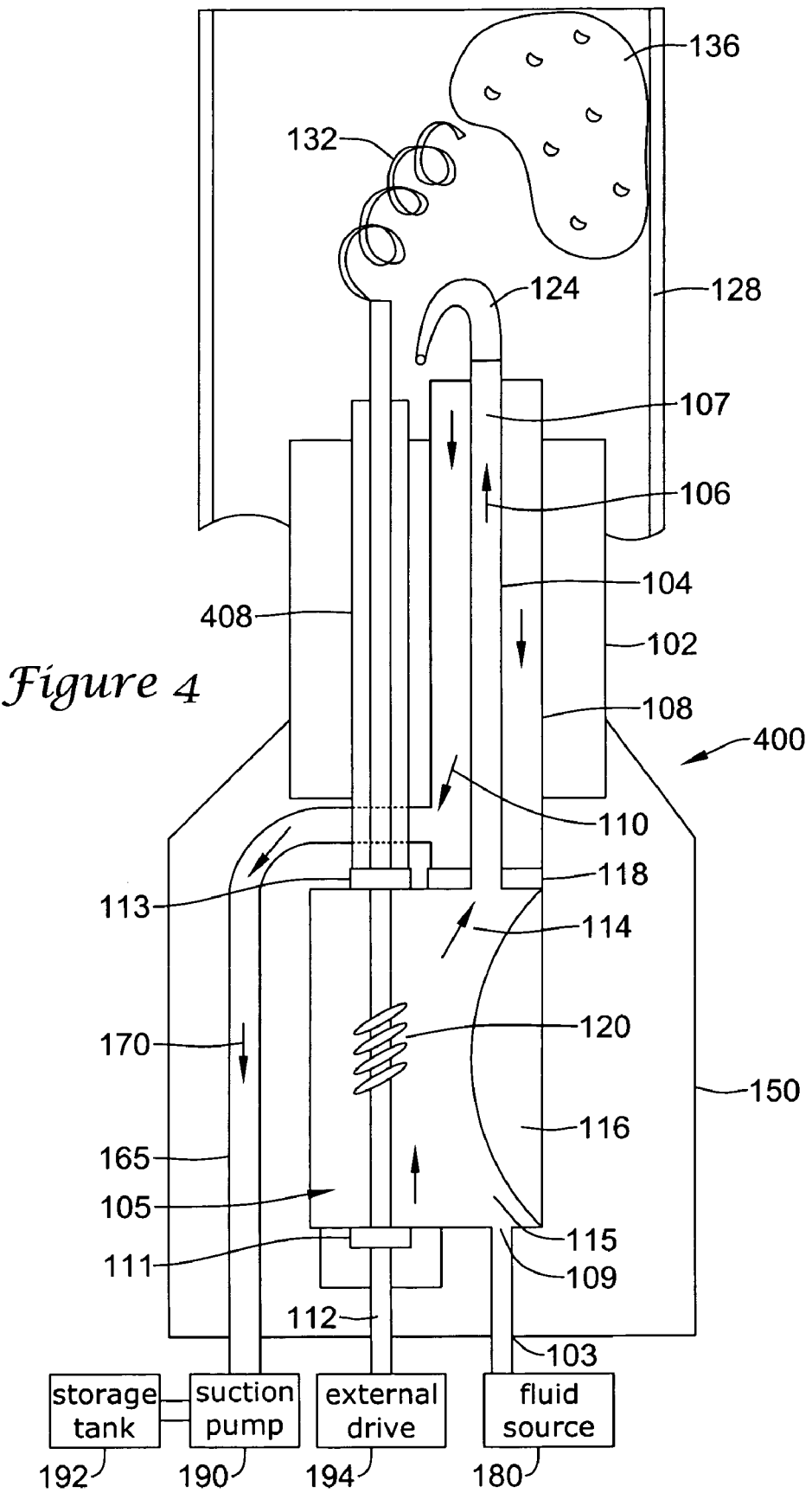
FIG. 4 is a longitudinal sectional view with a partial schematic, showing still other exemplary embodiments of the apparatus and system of the present invention.

FIG. 4 illustrates yet another embodiment of the invention. The distal flow of fluid as indicated by arrows 114 is directed from chamber 115 into an inlet fluid input tube 107, which can be said to define the first channel 104, which is disposed within the second channel 108. Inlet fluid tube 107 may be a tube comprised of polyimide. Fluid flow continues in a distal direction to nozzle 124 as indicated by the arrow in fluid flow path 106. Nozzle 124 is configured to connect to inlet fluid tube 107 at its proximal end and then has a tight bend back toward its attachment point on tube 107. The purpose for the tight turn of nozzle 124 in the proximal direction is so that the flow of fluid is directed back into the return fluid flow path 110. Return fluid flow path has an annular shape within first channel 104 around tube 107. Nozzle 124 progressively turns back on itself and simultaneously has a reduction of the diameter from that of tube 107 to a relatively minute opening at the tip. The function of the shape and direction of the nozzle is as similarly stated in previous exemplary embodiments. In the present embodiment, however, the micro-fragmented macerated thrombus 170 enters into channel 108 and then traverses into fluid return tube 165. Again, tube 165 is similar to tube 160 of previous embodiments. In the present embodiment, suction pump 190 may be used to provide suction to assist effluent 170 out of tube 165 into storage tank 192. Guidewire 112 is disposed within third channel 408, as shown.

In general, operation of apparatus for removal of thrombus 136 from a blood vessel 128 of the human body for devices 100, 200, 300, and 400 is similar and is described as follows: The flexible catheter 102 is advanced through the artery to the site of the obstruction, e.g. thrombus. The flexible catheter 102 is then adjusted until the tip portion 132 is located immediately adjacent the restriction. The plurality of fins 120 attached to the guidewire 112 is then rotated by the impacting fluid as shown by the flow path 114. The fluid enters channel 104 as the tip portion 132 rotates. Any particles or emboli of the thrombus cut away by the rotating tip 132 become macerated or micro-fragmented by the fluid from nozzle 124. The fluid is restricted from flowing distally of the restriction because suction is applied to return fluid flow path 110, and preferably because fluid direction nozzle 124 creates a Venturi effect that causes the micro fragmented particles of macerated thrombus to mix with fluid and enter return fluid flow path 110. Debris created by the restriction opening process is aspirated by the fluid when the fluid is sprayed out of channel 104 through nozzle 124.

One skilled in the art should be aware that the catheter described heretofore have inherent limitations insofar as the physical size and radius of passageways, e.g., arteries, which can be negotiated to locate the tip portion 132 at the site of a restriction to be opened. It is practical, however, to remove obstructions located in very small arteries or other lumen located a substantial distance from the point at which the catheter is to be introduced with a self rotating flexible wire tip portion. In this regard, the device for dislodging a wall adherent thrombus described herein is a rotary self-driven intravascular thrombus removing catheter that simultaneously washes away the effluent from the area. The catheter may include a self-powered guidewire, like that described above, which is driven by the force of fluid impacting on the plurality of fins 120 attached to one segment of the guidewire 112. As a supplemental rotary or axial driver, alternative methods such as pneumatically, hydrodynamically, and electrically powered drive units, with the power located at the proximal end of the catheter, can be used.

Figure 5:
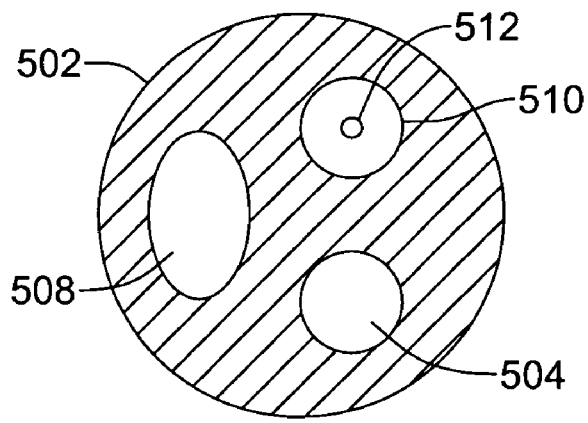
FIG. 5 is a cross-sectional view of a catheter according to another embodiment of the invention.

In some medical applications, it may be desirable to use a catheter with a channel or passage dedicated solely to containing the guidewire, with no fluid flowing therein. FIG. 5 shows a cross-sectional view of such a catheter 502 having a first channel 504, a second channel 508, and a third channel 510. All other aspects of the apparatus and system contemplated by FIG. 5 are the same as those shown in FIGS. 1–4. Therefore, the apparatus may also include a guidewire 512 longitudinally extending through third channel 510 and having a tip portion extending beyond the distal end of catheter 502 for dislodging an obstruction upon rotation. The apparatus also includes a drive system for rotating guidewire 512 to cause the tip portion to dislodge the obstruction, as shown in FIGS. 1–4 and discussed above. First channel 504 accommodates an inlet fluid flow path from proximal end of catheter 502 towards the distal end for providing pressurized fluid into the lumen. Second channel 508 accommodates a return fluid flow path from the distal end of catheter 502 towards the proximal end. Preferably, the cross-sectional area of second channel 508 is greater than that of first channel 504 to facilitate the aspiration of the effluent and the development of a Venturi effect. Also, although FIG. 5 shows channels formed in an otherwise solid catheter 502, the channels could be formed by the placement of tubes in a hollow catheter, as mentioned above.

As illustrated in FIGS. 6–21, a variety of shapes can be used for tip portion 132. Some of the tips are configured to generate a half sine wave function (single node) so as to cause a dislodging effect during rotation of guidewire 112 which will tend to break up thrombus more efficiently but not adversely affect the lumen in which the thrombus or other obstruction resides. In some cases, a larger degree of curvature in the tip portion allows the tip to adapt better to the surrounding lumen, such as a body lumen wall.

Figure 6:
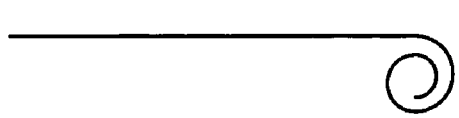
FIGS. 6–21 illustrate various embodiments of the tip portion used in connection with the apparatus of the present invention.
Figure 9:
Figure 7:
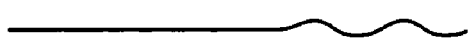
Figure 10:
Figure 8:
Figure 11:
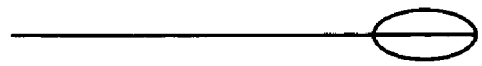
Figure 12:
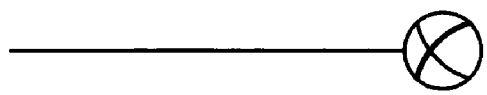
Figure 16:
Figure 13:
Figure 17:
Figure 14:
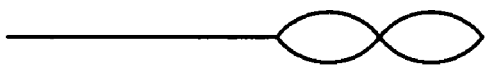
Figure 18:
Figure 15:
Figure 19:

Referring to FIGS. 6–21, a description of the varied configurations of the tip portion 132 follows: FIG. 6 (coiled distal tip) starts at a proximal end having a straightened segment of guidewire with the tip portion then bending inwardly in an increasingly tighter spiral at the distal end; FIG. 7 (one plane wavy distal tip) starts at a proximal end having a straightened segment of guidewire with the tip portion then rising and falling twice creating in a single plane wave-like perturbations at the distal end; FIG. 8 (two plane wavy distal tip) starts at a proximal end having a straightened segment of guidewire with the tip portion then having a wave in a first plane and then a wave in a second plane 90 degrees offset from the first plane (i.e., into the page of FIG. 8) creating two plane wave-like perturbations at the distal end, with the planes of the waves perpendicular to each other; FIG. 8 can also be viewed as having curves and straight segments; FIG. 9 (Multiple coil/loop distal tip) starts at a proximal end having a straightened segment of guidewire with the tip portion then bending to form three (or more) coils or loops of equal radius at the distal end; FIG. 10 (loop, oval distal tip) starts at a proximal end having a straightened segment of guidewire with the tip portion then rising then bending elliptically back toward the proximal end meeting at the origin of the bend to form an oval or loops of equal radius at the distal end; FIG. 11 (basket distal tip) starts at a proximal end having a straightened segment of guidewire with the tip portion in a first plane rising then bending elliptically back toward the proximal end meeting at the origin of the bend then in a second plane (90 degrees offset from the first plane) repeating a second elliptical formation to form an oval basket at the distal end; FIG. 12 (ball distal tip) starts at a proximal end having a straightened segment of guidewire with the tip portion in a plurality of planes bending and following a circular radius back toward the proximal end, with each circular radius closing the circumference at the origin of the bend to form a spherical ball at the distal end; FIG. 13 (helical distal tip) starts at a proximal end having a straightened segment of guidewire with the tip portion then bending to form three coils with each succeeding coil having a decreasing radius at the distal end; FIG. 14 (multi-helical distal tip) starts at a proximal end having a straightened segment of guidewire then the tip portion in a first plane bending to form three coils with each succeeding coil having a decreasing radius and at the distal end bending in a second plane and forming three coils with each succeeding coil having increasing radius and terminating where the first coil started; FIG. 15 (½ sine plain distal tip) starts at a proximal end increasing in a sinusoidal fashion having termination of a plain distal tip (i.e., a tip merely ending with a cut wire); FIG. 16 (½ sine open loop-back distal tip or a ball weld tip) starts at a proximal end increasing in a sinusoidal fashion and at the distal end bending back on itself to form a termination of an open loop distal tip; FIG. 17 (½ sine closed loop-back distal tip or a ball weld tip) starts at a proximal end increasing in a sinusoidal fashion and at the distal end bending back on itself forming an open loop that is filled in with a non toxic, adhering, self-hardening material to form a termination of a closed loop distal tip; FIG. 18 (½ sine plain short distal tip) starts at a proximal end increasing in a sinusoidal fashion and having a shortened length with plain distal tip following the positive sinusoidal amplitude rise; and FIG. 19 (full sine plain short distal tip) starts at a proximal end increasing in a sinusoidal fashion and having a shortened length with plain distal tip following the sinusoidal pattern. Although not shown, the guidewires of FIGS. 15–19 may also have a segment of straight guidewire attached to the tip portions and extending beyond the distal end of catheter 102 in operation.

Figure 20:
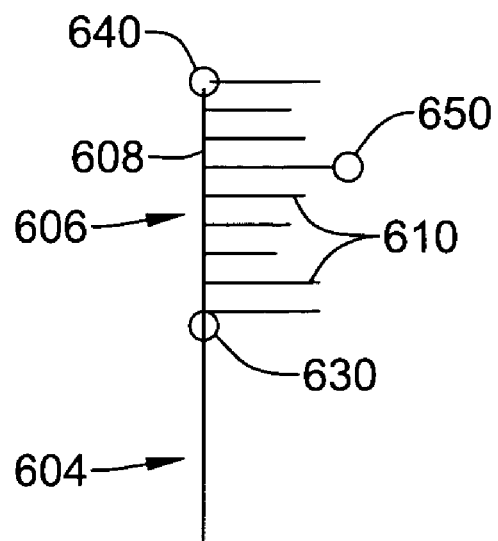
Figure 21:
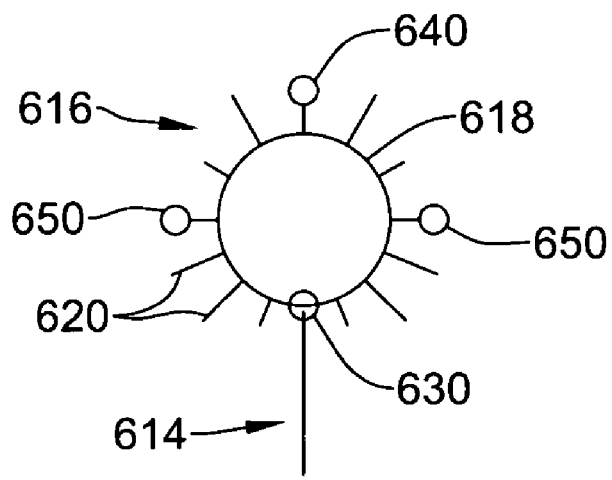

FIG. 20 shows a guidewire comprising a segment of a straight portion 604 and a tip portion 606 comprising a base filament 608 and a plurality of cutting filaments 610 extending perpendicularly from the base filament. This is a "brush" configuration of the tip portion. Although shown as extending in only one direction, the cutting filaments 610 may extend in additional radial directions from base filament 608. FIG. 21 shows a guidewire comprising a segment of a straight portion 614 and a tip portion 616 comprising a circular element 618 and a plurality of cutting filaments 620 extending radially outward from the circular element. The element from which the filaments extend could also be ovular.

FIGS. 20 and 21 also show radiopaque markers 630, 640, and 650 formed on the tip portions. The materials which may be used for such radiopaque markers and the manner in which they are attached to devices are well known in the art. As shown in FIGS. 20 and 21, a first radiopaque marker 630 is placed at the proximal end of the tip portion 606 or 616 and a second radiopaque marker 640 is placed at the distal end of the tip portion. In this way, a medical professional can identify the axial range over which some cutting will be achieved. Preferably, radiopaque markers 650 are also disposed at the radially outermost points of the cutting filaments 610 or 620 (i.e., the longest cutting filament of FIG. 20 and the central cutting filaments of FIG. 21). In this way, a medical professional can more easily detect the radial limits over which some cutting will be achieved.

Although many more shapes can be described similar to those described herein above, it is understood that the amplitude, degree of curvature and position of the peak amplitude with respect to the proximal and distal ends of the tip portion can be varied to suit the pattern of removal desired by the rotating tip. The various shapes give various three dimensional profiles when rotated, thus producing different types of agitation to wall adherent thrombus. The distal segment configurations shown have exposed ends, curved ends, and ball tipped ends. Another possibility is to polymer coat the distal segment to provide protection from the distal tip. The polymer could also be loaded with a radiopaque filler for visibility of the agitator segment. Other coatings can be used to aid in dissolving the obstruction.

This distal segment can also be tapered. The taper should be short enough so that the shaft stays stiff, while also being long enough to provide flexibility at the agitator distal configuration to adjust to the lumen, such as a body lumen, and also be retracted into the catheter. Many tapers can be used, but a good starting point is a taper length equal to the maximum distance the agitator distal end would protrude from the catheter. A tip portion could be constructed of wire, multi-strand cable, coil, or multi-wire coil. As discussed above, the distal tip of tip portion could be bent over, coated to prevent clotting, formed, welded into a ball or left natural (i.e., a plain distal tip). The material could be a metal such as, stainless steel, nitinol, or a polymer. A combination of materials is also a possibility. The device could also be coated to reduce friction with Teflon® (fluoropolymer resin), DLC (Diamond-Like Carbon), paralyene, or other suitable coating.

Although the invention is described in connection with certain preferred embodiments for the particular purpose of removing thrombus, it will be evident to those skilled in the art that the method and apparatus of the invention has application for treatment of other conditions. Moreover, the described method and technique for the removal of thrombus is not limited to any particular texture of tissue and is applicable to all atherosclerotic processes and others. It is further contemplated that the method and apparatus of the invention will have applications outside of human medicine as well as many applications for treatment of many conditions in the human body. Obviously, the specific size and design of the catheter, fluid directing tip, tip portion, and the specific design of the rotating fins will depend upon the particular application of the invention. Having thus described the invention, it will be obvious to those skilled in the art that various revisions and modifications can be made to the preferred embodiments described herein without departing from the spirit and scope of the invention. All such revisions and modifications as are obvious to those skilled in the art will be included within the scope of the following claims.

What is claimed:

1. An apparatus for removing an obstruction from inside of a lumen, comprising:
   a catheter defining a first fluid pathway and a second fluid pathway, wherein at least a portion of said catheter is adapted for insertion into the lumen, said first pathway accommodates an inlet fluid flow path from a proximal portion of the catheter towards a distal end of the catheter for providing pressurized fluid into the lumen, and said second pathway accommodates a return fluid flow path from said distal end of said catheter towards said proximal end;
   wherein the first fluid pathway consists of a first channel and the second fluid pathway consists of a second channel;
   a guidewire longitudinally extending through said catheter and having a tip portion extending beyond said distal end of said catheter for dislodging the obstruction upon rotation;
   means for rotating said guidewire to cause said tip portion to dislodge the obstruction; and
   a nozzle formed at the distal end of said first channel for extending into said lumen and configured to direct pressurized fluid to said lumen and said return fluid flow path.

2. The apparatus of claim 1 further comprising an inlet fluid tube which defines said inlet fluid flow path and is disposed in said first channel, and wherein said guidewire is disposed in said second channel.

3. The apparatus of claim 1, wherein said tip portion is retractable into said catheter for aiding introduction of said catheter into the lumen.

4. The apparatus of claim 1, wherein said tip portion and a segment of a straight portion of said guidewire extend beyond the distal end of said catheter in operation.

5. The apparatus of claim 4, wherein said tip portion has a shape selected from the group consisting of a spiral, a curve, a sine wave, a straight section, a multiplane sine wave, a multiple coil, an oval, a basket comprising a plurality of ovals, a sphere comprising a plurality of circles, a helix, a half sine wave, and a multi-helix.

6. The apparatus of claim 5, wherein said tip portion has a termination selected from the group consisting of a plain distal tip, an open loop distal tip, a closed loop distal tip, and a ball weld distal tip.

7. The apparatus of claim 4, wherein said tip portion has a termination selected from the group consisting of a plain distal tip, an open loop distal tip, a closed loop distal tip, and a ball weld distal tip.

8. The apparatus of claim 4, wherein said tip portion comprises a base filament and a plurality of cutting filaments extending perpendicularly from said base filament.

9. The apparatus of claim 4, wherein said tip portion comprises a circular element and a plurality of cutting filaments extending radially outward from said circular element.

10. The apparatus of claim 4, wherein said tip portion has a proximal end and a distal end and a first radiopaque marker at the proximal end of said tip portion and a second radiopaque marker at the distal end of said tip portion.

11. The apparatus of claim 4, wherein said tip portion has a radiopaque marker at a radially outermost point of said tip portion.

12. The apparatus of claim 1, wherein said means for rotating said guidewire comprise an external driver coupled to said guidewire.

13. The apparatus of claim 12, wherein said external driver is selected from the group consisting of a pneumatic driver and an electrical driver.

14. The apparatus of claim 1, wherein said catheter has a diameter of five to seven french.

* * * * *